United States Patent [19]

Tindall

[11] 4,252,798

[45] Feb. 24, 1981

[54] REVERSIBLE MALE CONTRACEPTION

[75] Inventor: Donald J. Tindall, Houston, Tex.

[73] Assignee: The Upjohn Company, Kalamazoo, Mich.

[21] Appl. No.: 121,543

[22] Filed: Feb. 14, 1980

Related U.S. Application Data

[63] Continuation of Ser. No. 949,799, Oct. 10, 1978, abandoned.

[51] Int. Cl.³ ............................................. A61K 31/58
[52] U.S. Cl. .................................. 424/241; 260/239.5; 260/397.4
[58] Field of Search ...................... 424/241; 260/239.5

[56] References Cited

U.S. PATENT DOCUMENTS

| | | | |
|---|---|---|---|
| 3,682,898 | 8/1972 | Klimstra | 260/239.5 |
| 3,704,295 | 11/1972 | Clinton | 260/239.5 |
| 3,754,086 | 4/1973 | Fujisawa | 260/239.5 |
| 3,846,456 | 11/1974 | Campbell et al. | 260/397.3 |

*Primary Examiner*—Elbert L. Roberts
*Attorney, Agent, or Firm*—Bruce Stein

[57] ABSTRACT

Various steroids which have a high affinity for rat ABP (androgen binding protein) and a low affinity for rat AR (androgen receptor) have been found to be useful as male contraceptives. Upon cessation of administration of the steroids of the present invention the male promptly regains normal fertility.

12 Claims, No Drawings

REVERSIBLE MALE CONTRACEPTION

This is a continuation, of application Ser. No. 949,799, filed Oct. 10, 1978, abandoned.

BACKGROUND OF THE INVENTION

Most forms of reversible contraception are practiced by the female member of an animal pair, whether the animal be human or not. With humans, physical (diaphragm and IUD) and chemical ("the Pill", vaginal creams, foams, ointments, etc.) methods are available. At present there are only two acceptable methods for the human male. These are the condom and bilateral vasectomy. With the condom the failure rate is high, resulting in unwanted pregnancies. Vasectomies for practical purposes must be considered irreversible. Therefore, a method of male human contraception which is both reversible and reliable is highly desirable.

With regards to the non-human mammals a male contraceptive is also highly desirable. For non-domestic commercial animals such as horses, cattle, sheep, etc., the present situation is to separate male and female animals so the female may be selectively, artificially inseminated. It would, of course, be simpler to permit the animals to cohabitate under circumstances where the female cannot become pregnant. Domestic animals normally cohabitate because it is virtually impossible to separate male and female cats and dogs in a household. Many times it would be desirable to be able to prevent unwanted pregnancies of domestic animals under cohabitation circumstances. Additionally, with undesirable rodents a male contraceptive would be helpful to decrease breeding and thereby decrease or eliminate the undesirable rodents.

E. Steinberger et al., Fertility and Sterility 27, 216 (1976), reported azoospermia in men who acknowledged paternity, by administration of testosterone enanthate. J. Mauss et al., Acta. Endocrinol. 78, 373 (1975) reported testosterone enanthate reduced the sperm count of seven men to less than 3,000,000 sperm/ml. Testosterone and testosterone enanthate are not within the scope of the compounds of the present invention because they are androgenic and the users would experience the known side effects of androgens including prostate enlargement, seminal vesicle enlargement, excess and unwanted hair growth and behavioral disturbances. The steroids within the scope of the present invention are much less androgenic as defined by these classical measures of androgenicity and by the ABP/AR ratio.

Howard C. Morse et al., J. Clin. Endocrinol. Metab., 37, 882 (1973) reported administering testosterone propionate to six normal men and found a decrease in testicular testosterone as well as a sharp drop in sperm concentration. Not only is testosterone propionate not within the scope of the present invention, but the publication does not even infer that the sperm level is decreased to the point that testosterone propionate is a contraceptive agent.

C. A. Paulsen and John M. Leonard, in Clinical Trials in Reversible Male Contraception: I, Combination of Danazol Plus Testosterone in Regulatory Mechanisms of Male Reproductive Physiology, C. H. Spilman et al., Editors, Excerpta Medica, Amsterdam, 1976, page 197 describe a Danazol-testosterone combination which ". . . represents a viable pathway for the purpose of inducing a reversible state of male infertility." Testosterone is known to produce undesired androgenic side effects.

U.S. Pat. No. 3,655,889 discloses a method of controlling the propagation of rodents by oral administration of quinesterol to both males and females. Quinesterol, an estrogen-type (aromatic A ring) steroid, is not within the scope of the present invention which utilizes non-estrogenic-type steroids (A ring is not aromatic).

U.S. Pat. No. 3,873,701 discloses using O-aryl oximes of testosterone-type compounds post-coitally in the female for suppression of reproduction. The compounds of the present invention are used in the male prior to sexual intercourse.

U.S. Pat. No. 4,000,273 discloses the use of 7α-methylestr-4-ene-3α,17β-diol-type compounds to reduce fertility in female mammals. The present invention involves contraceptives in males.

U.S. Pat. No. 3,846,456 discloses the use of various 2α,7α-dimethyltestosterone-type steroids for various uses including anti-fertility. However, these compounds have substantial androgenic side effects. The male contraceptive steroids of the present invention have minimal androgenic side effects (low affinity for AR). 2α,-7α-Dimethyltestosterone had an ABP/AR ratio of about 6.0.

SUMMARY OF THE INVENTION

Disclosed is a method of effecting male contraception which comprises oral administration of a contraceptively effective amount of a non-estrogenic steroid which has an ABP/AR ratio greater than 100 (male contraceptive steroid) to a healthy male mammal post-puberty selected from the group consisting of man, male dog, tom, bull, stallion, ram, boar, male rate and male mouse.

It is preferred that the male contraceptive be selected from the group consisting of compounds of the formula:

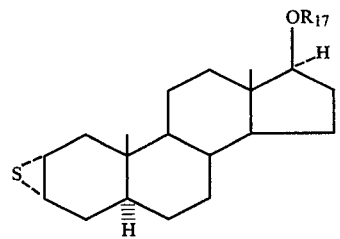

or 17β-methoxy-2α-methyl-5α-androstan-3-one.

It is more preferred that the male contraceptive steroid be selected from the group consisting of 17β-methoxy-2α-methyl-5α-androstan-3-one, 2α,3α-epithio-17β-methoxy-5α-androstane, and 2α,3α-epithio-17β-ethoxy-5α-androstane.

It is preferred that the healthy male mammal post-puberty be man.

It is preferred that the ABP/AR ratio be greater than 200. It is more preferred that the ABP/AR ratio be greater than 300.

It is preferred that the contraceptively effective amount of the male contraceptive steroid be about 0.01 to about 15 mg./kg./day.

17β-Methoxy-2α-methyl-5α-androstan-3-one is known. See Acta. Endo. 36, 83 (1961).

2α,3α-Epithio-17β-hydroxy-5α-androstane 17-methyl, ethyl and tetrahydropyranyl ethers are known.

See U.S. Pat. No. 3,301,850, Examples 18, 19 and 8, respectively.

DETAILED DESCRIPTION OF THE INVENTION

The present invention includes steroids which have a high affinity for rat ABP (androgen binding protein) as compared to DHT (dihydrotestosterone, 17β-hydroxy-5α-androst-3-one). N. A. Musto et al. in Endo. Res. Comm. 4, 147 (1977) have described a procedure for isolation and purification of rat ABP. Utilizing the purified rat ABP, and following the procedure of E. M. Ritzen et al. described in J. Biol. Chem. 249, 6597 (1974), the relative affinity of various non-estrogenic-type steroids can readily be determined. The dissociation constant ($K_d$) measures the affinity of a compound for a protein. The dissociation constant for DHT and the non-estrogenic-type steroids is determined. The dissociation constants for the steroids is then compared to the dissociation constant for DHT to obtain the relative affinity of the steroids for rat ABP as compared to DHT.

E. M. Wilson and F. S. French in the J. Biol. Chem. 251, 5620 (1976) have described a procedure for isolation and partial purification of rat AR. Utilizing the rat AR and following the procedure of G. Verhoeven et al. described in Steroids 26, 149 (1975) the relative affinity of various steroids can readily be determined. The dissociation constant for DHT and non-estrogenic steroids is determined. The dissociation constants for the steroids is then compared to the dissociation constant for DHT to obtain the relative affinity of the steroids for rat AR as compared to DHT. D. J. Tindall, et al., in the International Journal of Andrology, Supplement 2 (1978) set forth the preferred method for determining the relative affinities of a steroid for ABP and AR from which the ABP/AR ratio can be calculated.

A ratio of the relative affinity of a non-estrogenic-type steroid for ABP and AR is determined. U.S. Pat. No. 3,846,456 disclosed that 2α,7α-dimethyltestosterone was useful as a male anti-fertility agent. It has been determined that 2α,7α-dimethyltestosterone has an ABP/AR ratio of about 6.0. The male contraceptive steroids of the present invention surprisingly and unexpectedly have an ABP/AR ratio of greater than 100. It is preferred that the ABP/AR ratio of greater than 200 and it is more preferred that the ABP/AR ratio be greater than 300.

The male contraceptive steroids (I) of the present invention are either known to those skilled in the art or can readily be prepared by known methods from compounds known to those skilled in the art. See U.S. Pat. No. 3,301,850, in particular Examples 18 and 19. 17β-Methoxy-2α-methyl-5α-androstan-3-one is known, see Acta Endo 36, 83 (1961).

The male contraceptive steroids of the present invention may be used either individually or in combination with each other in the method of treatment of the present invention.

The method of the present invention is used to provide reversible contraception for male mammals post puberty which are selected from the group consisting of man, male dog, tom, bull, stallion, ram, boar, male rat, and male mouse.

With regards to the human, there are many instances in which the female cannot take various types of chemical contraceptive agents and does not with or cannot use various physical contraceptive devices such as IUD (IUCD) or diaphragm. In addition, many women do not wish to rely on non-prescription (over-the-counter) foams, gels and cream chemical contraceptive agents. Therefore, there are numerous instances in which it would be highly desirable to have a reliable reversible contraceptive agent for men. This is particularly true in view of the fact that the only reversible contraceptive agent for man is a mechanical device (prophylactic) which has the distinct disadvantage of low efficacy. In addition, there is the disadvantage of mechanical devices of having to interrupt intercourse to properly position the device.

The useful warm blooded animals can be divided into 2 groups—domesticated (dog, tom) and commercial (bull, stallion, ram and boar). The domesticated male animals usually cohabitate with the females. The commercial male animals are usually separated from the females because either it is desired that the particular males not fertilize the females so that artificial insemination may be used or even if the particular males are well suited to fertilizing the females it may be desired that they not do so at the present time. The use of the methods of the present invention permits one to allow both the domestic and commercial male and females to cohabitate without sterilization of either sex and without unwanted pregnancies and still retain the flexibility of fertilizing the female when desired either with a desired male or by artificial insemination.

With regards to the rodents, the rat and mouse, it is highly desirable of course to be able to eradicate or control the populations of these rodents with the methods of the present invention. These rodents can be controlled and/or eradicated by decreasing the fertility of these rodents by use of the methods of the present invention. This of course would not eliminate the rodents which are present, but only future rodents which these animals might conceive thereby decreasing future populations of these undesirable animals.

While testosterone and some of its derivatives have been suggested and tried in man as contraceptives in the past, these agents had the distinct disadvantage of typical androgenic side effects which include prostate enlargement, seminal vesicle enlargement, excess and unwanted hair growth and behavioral disturbances. The compounds used in the compositions and methods of treatment of the present invention surprisingly and unexpectedly cause male contraception without causing the typical unwanted androgenic side effects when given in the effective dose range.

The male contraceptive steroids of the present invention are administered such that the male mammal receives about 0.01 to about 15 mg./kg./day. For a 70 kg. male the amount would be about 0.7 mg. to about 1,050 mg./day.

Since the male contraceptive steroids must be in the blood stream daily to be effective it can be administered daily by tablet, capsule, liquid, treat, bait or veterinary premix incorporated into an animal's feed.

The exact dose of the male contraceptive steroid will depend on the particular compound, the weight, age, physical condition and particular patient to be treated.

The male contraceptive steroid is administered in a pharmaceutical composition of the following types: tablets, capsules, liquids (elixirs, syrups, suspensions, emulsions), treats, bait, veterinary premix and animal feed.

Various types of tablets and capsules are known to those skilled in the art for formulating pharmaceutical compositions for use by man.

Types of oral tablets are, for example, compressed (including chewable and lozenge), tablet triturates, enteric-coated, sugar-coated, film-coated, and multiple compressed. Capsules are either hard or soft elastic gelatin.

Pharmaceutically acceptable substances utilized in compressed tablets are binders, lubricants, diluents, disintegrating agents, coloring agents, flavoring agents, flow-inducing agents, and wetting agents. Tablets triturates (either molded or compressed) utilize diluents and binders. Enteric-coated tablets, due to their enteric-coating, resist the action of stomach acid and dissolve or disintegrate in the alkaline intestine. Sugar-coated tablets are compressed tablets to which usually four different layers of pharmaceutically acceptable substances have been applied. Film-coated tablets are compressed tablets which have been coated with a water soluble cellulose high polymer. Multiple compressed tablets are compressed tablets made by more than one compression cycle utilizing the pharmaceutically acceptable substances previously mentioned. Coloring agents are utilized in all the above dosage forms. Flavoring and sweetening agents are utilized in compressed tablets, tablet triturates, sugar coated, multiple compressed and chewable tablets. Flavoring and sweetening agents are especially useful in the formation of chewable tablets and lozenges.

Examples of binders include glucose solution (25–50), acocia mucilage (10–20%), gelatin solution (10–20%), sucrose and starch paste. Lubricants include, for example, talc, starch, magnesium or calcium stearate, lycopodium and stearic acid. Diluents include, for example, lactose, sucrose, starch, kaolin, salt, mannitol and dicalcium phosphate. Disintegrating agents include, for example, corn starch, potato starch, bentonite, methylcellulose, agar and carboxymethylcellulose. Coloring agents include, for example, any of the approved certified water soluble FD and C dyes, mixtures thereof, and water insoluble FD and C dyes suspended on alumina hydrate. Sweetening agents include, for example, sucrose, lactose, mannitol, and artificial sweetening agents such as sodium cyclamate and saccharin, and any number of spray dried flavors. Flavoring agents include natural flavors extracted from plants such as fruits and synthetic blends of compounds which produce a pleasant sensation. Flow inducing agents include, for example, silicon dioxide and talc. Wetting agents include, for example, propylene glycol monostearate, sorbitan monoleate, diethylene glycol monolaurate and polyoxyethylene lauryl ether. Enteric-coatings include, for example, fatty acids, fats, waxes, shellac, ammoniated shellac and cellulose acetate phthalates. Pharmaceutically acceptable substances for the first layer, an undercoating, of sugar-coated tablets include, for example, dextrin and gelatin. The second layer, an opaque zone, includes, for example, starch, talc, calcium carbonate, magnesium oxide and magnesium carbonate. The third layer, a translucent zone, includes, for example, sucrose. The fourth layer, a glaze, includes, for example, beeswax, carnauba wax, or a mixture of these waxes. Film coatings include, for example, hydroxyethylcellulose, sodium carboxymethylcellulose, polyethylene glycol 4000 and cellulose acetate phthalate.

Hard gelatin capsules, sizes 5 thru 000, are made largely from gelatin and may be either clear or colored. These capsules may be filled with either a powder or coated pellets (sustained release).

The diluents utilized in powder filled capsules are the same as those illustrated above for tablets. Pharmaceutically acceptable substances utilized for coating pellets include, for example, stearic acid, palmitic acid, glyceryl myristate, cetyl alcohol, fats, waxes, polymeric substances sensitive to small changes in pH of the gastro-intestinal tract, polyvinyl alcohol, ethyl cellulose and mixtures of beeswax, carnauba wax or bayberry wax with glyceryl monostearate.

Soft elastic gelatin capsules contain sufficient glycerin so that they are permanently flexible. Pharmaceutically acceptable liquid diluents used in soft elastic gelatin capsules are those which do not dissolve or harm the capsule and which are non-toxic, including, for example, corn oil, cottonseed oil and polysorbate 80.

The individual oral solid pharmaceutical dosage forms, tablets and capsules, are packaged individually (unit-dose) or in quantity (multiple-dose containers), for example, bottles of 50, 100, 500, 1000, or 5000. The amount of the male contraceptive steroid per dosage unit (tablet or capsule) is adjusted so that a tablet or capsule, a fraction or multiple thereof, provides the patient with an effective amount. It is preferred that each tablet or capsule contains 1–250 mg. or the male contraceptive steroid. The exact dose depends on the particular compound, the age, weight, physical condition and the particular patient or animal as is known in the art. Tablets and capsules are given in sufficient number and frequency to obtain the desired pharmacological effect.

The sustained release tablets and capsules provide an effective amount and continue to release a sufficient amount of the male contraceptive steroid to keep the concentration of the active ingredient at an effective level for increased periods of time, for example, 12–24 hours.

U.S. Pat. No. 3,150,042 discloses a tablet formulation used to treat dogs, cats and rabbits.

Treats containing 1–200 mg. of the male contraceptive steroid for male dogs and toms are similar to tablets. They are discrete dosage units which carry an effective amount of the male contraceptive steroid for the particular animal to be treated. It must contain some flavoring agent which makes it especially attractive to the animal as is known in the art. There are numerous treats on the market for dogs and cats.

Many rodenticides are used in the form of bait. Some refer to this as ration, see U.S. Pat. No. 3,659,022. Bait is similar to treat in that it must be attractive to the male rat or male mouse and carry an effective amount of the male contraceptive steroid. Since rats and mice are smaller than dogs and cats bait will have a smaller amount of the male contraceptive steroid. Many commercial baits now in use may be used. The male contraceptive steroid may either be added to, or replace the active ingredient in the commercial baits. The formulation of bait is well known, see U.S. Pat. No. 3,655,889.

Liquid dosage forms containing 1–200 mg./ml. of the male contraceptive steroid can be used in many different ways. A human may take a fraction or multiple of a teaspoonful daily which contains an effective amount of the male contraceptive steroid. For dogs or cats, the liquid may be mixed with their daily feed. The liquid may be formulated as an elixir, syrup, suspension or emulsion as is well known to those skilled in the art. It is preferred that the liquid be a syrup especially when it is to be added to an animal's feed. For example, Cheque ® (mibolerone) is marketed by The Upjohn Company, Kalamazoo, Michigan.

Oral administration also utilizes a veterinary premix for the commercial and domesticated animals. This is an advantageous way to administer the male contraceptive steroids of the present invention to the animal's daily feed as is well known to those skilled in the art. See U.S. Pat. Nos. 3,150,042; 3,261,687; 3,245,797; and 3,482,023.

The feed carriers for domestic and commercial animals comprise in balanced amounts the essential dietary constituents protein, fat, carbohydrate, minerals, and the like. Premixes, for addition to animal feed, contain ingestible bulking agents or diluents which can be dietary constituents, and the male contraceptive steroids of the present invention in a concentration suited for addition to the animal's feed in amounts calculated on the weight of the animal under treatment.

The animal feed compositions should contain from about 0.0005 to about 0.3% (w/w) of the male contraceptive steroid of the present invention.

The veterinary premixes contain from about 0.05 to about 5% (w/w) of the male contraceptive steroids of the present invention. The veterinary premixes are added to the daily feed rations in amounts calculated to provide the male contraceptive steroids of the present invention in daily dosages of from about 0.01 to about 15 mg./kg.

A dry premix suitable for incorporation into the normal diet of dogs is prepared, for example, from the following types and amounts of ingredients:

|  | Kg. |
| --- | --- |
| Part I |  |
| Male Contraceptive Steroid | 1 |
| Liver protein | 64 |
| Whole liver powder | 60 |
| Fish meal | 200 |
| Terra alba | 24 |
| Dicalcium phosphate | 100 |
| Ferrous gluconate powder | 6½ |
| Part II |  |
| Lecithin | 32 |
| Wheat germ oil | 11½ |
| Brewer's yeast | 200 |

The Part I ingredients are mixed well together. The Part II wheat germ oil is mixed with the warmed lecithin and this mixture is added slowly to the brewer's yeast. The Part II mixture is then blended well with the Part I mixture to give the final product. Each 3.5 gms. (approximately 1 teaspoonful) of the final mixture contains 5 mgs. of the active ingredient. The proper amount of this premix to be added to the animal ration can be calculated from the weight of the animal, the required dosage of active ingredient, and the amount of food consumed per day. In Kirk's Index of Treatment in Small-Animal Practice, published in 1951 by The Williams and Wilkins Company, there is a table on page 713 of good requirements in dogs:

TABLE IV

| Food maintenance requirements of mature dogs | |
| --- | --- |
| Body Weight (Kg.) | Grams of Food per animal fresh basis (70 percent moisture) per day |
| 1 | 118 |
| 2 | 195 |
| 3 | 262 |

TABLE IV-continued

| Food maintenance requirements of mature dogs | |
| --- | --- |
| Body Weight (Kg.) | Grams of Food per animal fresh basis (70 percent moisture) per day |
| 4 | 323 |
| 5 | 380 |
| 6 | 433 |
| 7 | 487 |
| 8 | 537 |
| 9 | 583 |
| 10 | 630 |
| 20 | 1040 |
| 30 | 1410 |
| 40 | 1740 |
| 50 | 2043 |

Another table, Number V, is given on page 712 of the same publication:

TABLE V

The following table of approximate quantities of food per day, for maintenance of an adult animal in a well-nourished condition, is one which is considered fairly reliable as a general guide:

| St. Bernards, mastiffs, great danes | 2.5–4.5 lbs. |
| --- | --- |
| Collies, retrievers, alsations and similar | 1.5–2.5 lbs. |
| Greyhounds | 1.8–2.5 lbs. |
| Airedales, chows, bulldogs and similar | .8–1.5 lbs. |
| Fox terriers, welsh terriers, scotties, etc. | 8–12 ozs. |
| Pugs, poms, pekingese | 4–8 ozs. |
| Cats | 4–8 ozs. |

From the above tables the amount of premix to be added daily to the food can be calculated. For example, using Table IV, to the 1740 gms. of food per day for a 40 kg. animal, at a daily dosage of 0.5 mg. of active ingredient per kg. of body weight, 4 teaspoonfuls of food supplement are used.

Another example of a veterinary premix is

| Male Contraceptive Steroid | 300 gm. |
| --- | --- |
| Soybean meal | 9700 gm. |
| Chloroform, USP | 1500 ml. |
|  | 10,000 gm. |

A chloroform solution of the male contraceptive steroid is prepared and incorporated gradually and uniformly into the soybean meal. After adequate mixing the whole is vacuum dried to remove any trace of chloroform.

Each gm. of the premix contains 30 mgs. of the active ingredient. The premix is added to the standard ration of feed.

An equally satisfactory premix is prepared by omitting the chloroform and using mineral oil to facilitate the preparation of a uniform premix which is well suited for latter incorporation into the animal ration.

Ready-mixed feed may be prepared in the following manner:

| Commercial dog feed | 100 lbs. |
| --- | --- |
| Male Contraceptive Steroid | 400 mgs. |

The male contraceptive steroid is worked into a portion of the feed by careful mixing and the mix is incorporated uniformly into the remaining feed by milling. Each pound of the finished preparation contains 4 mgs. of the steroid providing a total daily dose of 5 mgs. for a 10 kilo dog eating 1¼ lbs. of the feed per day. This daily dose is effective in preventing conception.

The formulation of animal feed and veterinary premix for methods of treatment of the non-human animals is well within the knowledge and ability of those skilled in the art.

Regardless of which type of pharmaceutical composition or veterinary premix is used in the methods of treatment of the present invention, a period of pretreatment with the male contraceptive steroids is required. For the male contraceptive steroids of the present invention to exert their contraceptive effect, the male animal should be pretreated continuously for a minimum period of 30–90 days depending on the length of the animal's spermatogenic cycle. Following this pretreatment period the male animal may be safely mated with a female animal of the same species at the time of ovulation or estrus without conception taking place. In order to insure continued contraception after the pretreatment period the male animal must maintain a continuous and relatively uniform blood level of the male contraceptive steroids. Therefore, the male animal must continue to take daily doses (tablet, capsule, or veterinary premix).

Following cessation of the daily administration of the male contraceptive steroid contraception will be maintained for only a very short period, about 21 days. Gradually over a period of about 90 days the male animal's ability to fertilize the female partner returns to normal.

The definitions and explanations below are for the terms as used throughout the entire patent application including both the specification and the claims.
USP refers to United States Pharmacopeia.
NF refers to National Formulary.
ABP refers to rat androgen binding protein.
AR refers to rat androgen receptor.
DHT refers to dihydrotestosterone, 17$\beta$-hydroxy-5$\alpha$-androstan-3-one.
M is a methyl, methoxy, trifluoromethyl, hydroxyl, or nitro group or a hydrogen, fluorine, chlorine or bromine atom.
n is 0 thru 4.
q is 1 or 2 and when 2, the M's may be the same or different.
Healthy refers to an animal which may have medical problems but none that require the use of the steroids of the present invention for treatment thereof. Therefore, the use of the steroids of the present invention in the steroids of the present invention in the healthy mammal is solely for contraceptive purposes and not to treat a disease.
Post puberty means a mammal which has a sufficient quantity of healthy normal sperm which can fertilize a female of the same species.
Non-estrogenic steroid refers to a steroid which does not have an aromatic A ring and which does not have typical estrogen properties.
Pharmaceutically acceptable refers to those properties and/or substances which are acceptable to the patient or animal from a pharmacological-toxicological point of view and to the manufacturing pharmaceutical chemist from a physical-chemical point of view regarding composition, formulation, stability, patient acceptance and bioavailability.

EXAMPLES

Without further elaboration, it is believed that one skilled in the art can, using the preceding description, practice the present invention to its fullest extent. The following preferred specific embodiments are, therefore, to be construed as merely illustrative, and not limiting of the preceding disclosure in any way whatsoever.

EXAMPLE 1

A 70 kg. 25 year old man who demonstrates approximately 100 million apparently normal sperm/ml. of ejaculate is treated with a 10 mg. tablet of 17$\beta$-methoxy-2$\alpha$-methyl-5$\alpha$-androstan-3-one twice daily for about 100 days. After which time it is found that following sexual intercourse he does not fertilize a fertile female (who has previously delivered a child) at the most fertile time of her cycle. The steroid is continuously administered to the man twice daily and he remains infertile.

EXAMPLE 2

An 80 kg. 22 year old man who demonstrates approximately 90 million apparently normal sperm/ml. of ejaculate is treated with a 200 mg. capsule of 17$\beta$-methoxy-2$\alpha$-methyl-5$\alpha$-androstan-3-one four times daily for 60 days. After which time it is found that following sexual intercourse he does not fertilize a fertile female (who has previously delivered a child) at the most fertile time of her cycle. The steroid is continuously administered to the man 4 times daily and he remains infertile.

EXAMPLE 3

A 70 kg. 30 year old man who demonstrates approximately 95 million apparently normal sperm/ml. of ejaculate is given one-half teaspoonful/day of an elixir of 2$\alpha$,3$\alpha$-epithio-17$\beta$-methoxy-5$\alpha$-androstane (100 mg./ml.). After 60 days it is found that following sexual intercourse he does not fertilize a fertile female (who has previously delivered a child) at the most fertile time of her cycle. Upon continued daily administration of the same amount of the elixir he remains infertile.

EXAMPLE 4

A 60 kg. 26 year old man who is the admitted parent of 2 children is given one 50 mg. tablet daily of 17$\beta$-methoxy-2$\alpha$-methyl-5$\alpha$-androstan-3-one. After 60 days it is found that following sexual intercourse he does not fertilize the mother of his 2 children at the most fertile time of her cycle. The steroid is continuously administered daily and he remains infertile.

EXAMPLE 5

A 60 kg. 20 year old man is treated daily with one teaspoonful of a suspension of 2$\alpha$,3$\alpha$-epithio-17$\beta$-ethoxy-5$\alpha$-androstane (100 mg./ml.). After 60 days it is found that following sexual intercourse he does not fertilize a fertile female (who has previously delivered a child) at the most fertile time of her cycle. Upon further administration the patient remains infertile.

EXAMPLE 6

A 6 kg. tom who has previously sired offspring is given a treat daily containing 20 mg. of 17$\beta$-methoxy-2$\alpha$-methyl-5$\alpha$-androstan-3-one. After 60 days it is found that following sexual intercourse the animal does not fertilize an ovulating female (who has previously delivered young) at the time of her estrus. Upon continuous daily administration of the treat to the tom the animal remains infertile. Eighty days following cessation of administration of the treat, the tom, upon sexual intercourse, fertilizes the same ovulating female at the time of her estrus.

EXAMPLE 7

A 10 kg. dog who has previously sired offspring is treated by adding to its daily food ration as follows: A veterinary premix containing 2% of the active ingredient is added to the animal's daily normal dietary intake such that it provides sufficient quantity of the active material for contraceptive purposes. In the particular case, using a 2% veterinary premix 5 g. of the premix delivers 100 mg. of the contraceptive agent which provides for 10 mg./kg./day. After feeding 60 days on this type of diet it is found that following sexual intercourse the animal does not fertilize an ovulating female (who has previously delivered young) at the time of her estrus.

In addition to the active ingredient the veterinary premix includes liver protein, whole liver powder, fresh meal, terra alba dicalcium phosphate, ferrous gluconate powder, wheat germ oil, and brewer's yeast in sufficient quantity to provide a veterinary premix containing 2% of the active ingredient.

I claim:

1. A method of effecting male contraception which comprises oral administration of a contraceptively effective amount of 17β-methoxy-2α-methyl-5α-androstan-3-one to a healthy male mammal post-puberty selected from the group consisting of male dog, tom, bull, stallion, ram, boar, male rat and male mouse.

2. A method of effecting male contraception according to claim 1 wherein the contraceptively effective amount is about 0.01 to about 15 mg./kg./day.

3. A method of effecting male contraception according to claim 2 wherein the oral administration is of 1–250 mg., 1 thru 4 times daily.

4. A method of effecting male contraception according to claim 2 where the healthy male mammal is selected from the group consisting of male dog or tom.

5. A method of effecting male contraception according to claim 4 where the oral administration utilized is a tablet.

6. A method of effecting male contraception according to claim 4 where the oral administration utilized is a liquid.

7. A method of effecting male contraception according to claim 4 where the oral administration utilized is a treat.

8. A method of effecting male contraception according to claim 2 where the healthy male mammal is a male rat or male mouse.

9. A method of effecting male contraception according to claim 8 where the oral administration utilized is bait.

10. A method of effecting male contraception according to claim 2 where the healthy male mammal is a bull, stallion, ram, or boar.

11. A method of effecting male contraception according to claim 10 where the oral administration is with a dry veterinary premix.

12. A method of effecting male contraception according to claim 10 where the oral administration is with an animal feed.

* * * * *

UNITED STATES PATENT AND TRADEMARK OFFICE
CERTIFICATE OF CORRECTION

PATENT NO. : 4,252,798

DATED : February 24, 1981

INVENTOR(S) : John C. Babcock, J Allan Campbell, Thomas J. Lobl, Anthony R. Means, Bert W. O'Malley and Donald J. Tindall It is certified that error appears in the above—identified patent and that said Letters Patent is hereby corrected as shown below:

Cover Page: "Inventor: Donald J. Tindall" should read --Inventors: John C. Babcock, J Allan Campbell, Thomas J. Lobl, Anthony R. Means, Bert W. O'Malley and Donald J. Tindall--.
Column 2, line 34: "male rate" should read -- male rat --.
Column 3, line 68: "not with" should read -- not wish --.
Column 5, line 12: "Tablets" should read -- Tablet --.
Column 5, line 31: "(25-50)" should read -- (25-50%) --.
Column 5, line 32: "acocia" should read -- acacia --.
Column 5, line 52: "monoleate" should read -- monooleate --.
Column 12, line 4: "wherein" should read -- where --.
Column 12, line 7: "wherein" should read -- where --.

Signed and Sealed this

Twenty-fifth Day of May, 1993

Attest:

MICHAEL K. KIRK

*Attesting Officer*   *Acting Commissioner of Patents and Trademarks*